(12) United States Patent
Gennrich et al.

(10) Patent No.: US 8,974,519 B2
(45) Date of Patent: Mar. 10, 2015

(54) THERAPEUTIC AGENT DELIVERY SYSTEM, DEVICE AND METHOD FOR LOCALIZED APPLICATION OF THERAPEUTIC SUBSTANCES TO A BIOLOGICAL CONDUIT

(75) Inventors: David J. Gennrich, Madison, WI (US); Jeffrey A. McBroom, Champlin, MN (US); Kristina Tibesar Jensen, Chaska, MN (US); Jody Lee Rivers, Elk River, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 66 days.

(21) Appl. No.: 13/029,379

(22) Filed: Feb. 17, 2011

(65) Prior Publication Data

US 2011/0208221 A1 Aug. 25, 2011

Related U.S. Application Data

(60) Provisional application No. 61/306,206, filed on Feb. 19, 2010.

(51) Int. Cl.
  *A61F 2/07* (2013.01)
  *A61B 17/22* (2006.01)
  *A61F 2/90* (2013.01)
  (Continued)

(52) U.S. Cl.
  CPC ........... *A61B 17/22* (2013.01); *A61F 2250/003* (2013.01); *A61F 2250/0003* (2013.01); *A61F 2002/077* (2013.01); *A61L 2300/604* (2013.01); *A61F 2/07* (2013.01); *A61B 17/32037* (2013.01); *A61B 2017/00004* (2013.01); *A61B 2017/22002* (2013.01); *A61B 2017/22051* (2013.01); *A61B 2017/22061* (2013.01); *A61B 2017/22084* (2013.01); *A61F 2/90* (2013.01); *A61F 2250/0068* (2013.01); *A61M 37/0069* (2013.01);
  (Continued)

(58) Field of Classification Search
  CPC ................ A61F 2/07; A61F 2002/077; A61F 2250/003; A61F 2250/0068; A61L 2300/604
  USPC ............. 623/1.1, 1.11, 1.13, 1.16, 1.23, 1.25, 623/1.28, 1.29, 1.38, 1.42, 1.43, 1.44, 623/23.64–23.67, 23.7
  See application file for complete search history.

(56) References Cited

U.S. PATENT DOCUMENTS 5,234,457 A 8/1993 Andersen
5,324,261 A 6/1994 Amundson et al.
(Continued)

FOREIGN PATENT DOCUMENTS

JP 2009506876 2/2009
WO WO2009/069112 6/2009

OTHER PUBLICATIONS

International Search Report dated Apr. 12, 2011 from related PCT application No. PCT/US2011/025372.

*Primary Examiner* — David Isabella
*Assistant Examiner* — Suba Ganesan
(74) *Attorney, Agent, or Firm* — Winthrop & Weinstine, P.A.

(57) ABSTRACT

The invention provides a system, device and method for localized application of therapeutic substances within a biological conduit. In various embodiments, a dissolvable bag or bolus of at least one therapeutic agent is introduced and pressed and/or sealed against the wall of conduit. In other embodiments, dissolvable barbs formed from at least one therapeutic agent are ejected from a catheter by fluid pressure, embedding in the wall of conduit.

15 Claims, 6 Drawing Sheets

(51) Int. Cl.
  *A61M 37/00* (2006.01)
  *A61B 17/3203* (2006.01)
  *A61B 17/00* (2006.01)

(52) U.S. Cl.
  CPC . *A61F 2220/0016* (2013.01); *A61F 2230/0078* (2013.01); *A61F 2230/008* (2013.01)
  USPC ...................................................... 623/1.42

(56) References Cited

U.S. PATENT DOCUMENTS

| | | | |
|---|---|---|---|
| 5,423,851 A | 6/1995 | Samuels | |
| 5,423,885 A | 6/1995 | Williams | |
| 5,755,706 A | 5/1998 | Kronenthal et al. | |
| 5,873,852 A | 2/1999 | Vigil et al. | |
| 5,891,108 A | 4/1999 | Leone et al. | |
| 5,948,191 A | 9/1999 | Solovay | |
| 6,156,062 A | 12/2000 | McGuinness | |
| 6,379,382 B1 * | 4/2002 | Yang | 623/1.42 |
| 6,537,195 B2 | 3/2003 | Forman | |
| 6,626,950 B2 | 9/2003 | Brown et al. | |
| 6,726,923 B2 | 4/2004 | Iyer et al. | |
| 7,004,962 B2 | 2/2006 | Stinson | |
| 7,270,668 B2 | 9/2007 | Andreas et al. | |
| 7,323,008 B2 | 1/2008 | Kantor et al. | |
| 7,364,585 B2 | 4/2008 | Weber | |
| 7,632,307 B2 | 12/2009 | Pacetti et al. | |
| 2002/0165601 A1 | 11/2002 | Clerc | |
| 2004/0011356 A1 | 1/2004 | Sullivan | |
| 2004/0034332 A1 | 2/2004 | Uhland | |
| 2004/0249441 A1 * | 12/2004 | Miller et al. | 623/1.15 |
| 2005/0064009 A1 | 3/2005 | Bates | |
| 2005/0113904 A1 | 5/2005 | Shank et al. | |
| 2005/0187607 A1 | 8/2005 | Akhtar et al. | |
| 2005/0271701 A1 | 12/2005 | Cottone, Jr. et al. | |
| 2005/0277978 A1 | 12/2005 | Greenhalgh | |
| 2006/0009839 A1 * | 1/2006 | Tan | 623/1.38 |
| 2006/0122522 A1 | 6/2006 | Chavan et al. | |
| 2006/0149266 A1 | 7/2006 | Cordasco | |
| 2006/0266474 A1 | 11/2006 | Burnside et al. | |
| 2007/0042017 A1 | 2/2007 | Kutryk et al. | |
| 2007/0055352 A1 * | 3/2007 | Naimark et al. | 623/1.16 |
| 2007/0055364 A1 | 3/2007 | Hossainy et al. | |
| 2007/0067015 A1 | 3/2007 | Jones et al. | |
| 2007/0270940 A1 | 11/2007 | Doty | |
| 2008/0097575 A1 | 4/2008 | Cottone | |
| 2008/0103440 A1 | 5/2008 | Ferren et al. | |
| 2008/0103584 A1 | 5/2008 | Su et al. | |
| 2008/0125709 A1 | 5/2008 | Chang et al. | |
| 2008/0311172 A1 | 12/2008 | Schapira et al. | |
| 2009/0076448 A1 | 3/2009 | Consigny et al. | |
| 2009/0270906 A1 | 10/2009 | Hossainy | |

* cited by examiner

THERAPEUTIC AGENT DELIVERY SYSTEM, DEVICE AND METHOD FOR LOCALIZED APPLICATION OF THERAPEUTIC SUBSTANCES TO A BIOLOGICAL CONDUIT

BACKGROUND OF THE INVENTION

1. Field of the Invention

The invention relates to systems, devices and methods for treating biological conduits, e.g., blood vessels, with localized delivery of therapeutic agents.

2. Description of the Related Art

A variety of techniques and instruments have been developed for use in the removal or repair of tissue in biological conduits, e.g., without limitation, blood vessels and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes, leg pain and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patency of the opened artery. For non-calcified lesions, balloon angioplasty most often is used alone to open the artery, and stents often are placed to maintain patency of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patency of the artery.

Several kinds of rotational atherectomy devices have been developed for attempting to remove stenotic material. In one type of device, such as that shown in U.S. Pat. No. 4,990,134 (Auth), a burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently more than one size burr must be utilized to open an artery to the desired diameter.

U.S. Pat. No. 5,314,438 (Shturman) discloses another atherectomy device having a drive shaft with a section of the drive shaft having an enlarged diameter, at least a segment of this enlarged surface being covered with an abrasive material to define an abrasive segment of the drive shaft. When rotated at high speeds, the abrasive segment is capable of removing stenotic tissue from an artery. Though this atherectomy device possesses certain advantages over the Auth device due to its flexibility, it also is capable only of opening an artery to a diameter about equal to the diameter of the enlarged abrading surface of the drive shaft since the device is not eccentric in nature.

U.S. Pat. No. 6,494,890 (Shturman) discloses an atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. Since the enlarged eccentric section comprises drive shaft wires that are not bound together, the enlarged eccentric section of the drive shaft may flex during placement within the stenosis or during high speed operation. This flexion allows for a larger diameter opening during high speed operation, but may also provide less control than desired over the diameter of the artery actually abraded. In addition, some stenotic tissue may block the passageway so completely that the Shturman device cannot be placed therethrough. Since Shturman requires that the enlarged eccentric section of the drive shaft be placed within the stenotic tissue to achieve abrasion, it will be less effective in cases where the enlarged eccentric section is prevented from moving into the stenosis. The disclosure of U.S. Pat. No. 6,494,890 is hereby incorporated by reference in its entirety.

U.S. Pat. No. 5,681,336 (Clement) provides an eccentric tissue removing burr with a coating of abrasive particles secured to a portion of its outer surface by a suitable binding material. This construction is limited, however because, as Clement explains at Col. 3, lines 53-55, that the asymmetrical burr is rotated at "lower speeds than are used with high speed ablation devices, to compensate for heat or imbalance." That is, given both the size and mass of the solid burr, it is infeasible to rotate the burr at the high speeds used during atherectomy procedures, i.e., 20,000-200,000 rpm. Essentially, the center of mass offset from the rotational axis of the drive shaft would result in development of significant centrifugal force, exerting too much pressure on the wall of the artery and creating too much heat and excessively large particles.

Another method of treatment of occluded vessels may include the use of stents. Stents may be placed at the site of a stenosis and expanded to widen the vessel, remaining in position as a vessel implant.

No matter the technique used to open an occluded conduit, e.g., blood vessel, and restore normal fluid flow therethrough, one problem remains: restenosis. A certain percentage of the treated conduits and vessels will reocclude (restenose) after a period of time; occurring in as many as 30-40% of the cases. When restenosis does occur, the original procedure may be repeated or an alternative method may be used to reestablish fluid, e.g., blood, flow.

The relevant commonality shared by each of the above treatment methods is that each one results in some trauma to the conduit wall. Restenosis occurs for a variety of reasons; each involving trauma. Small clots may form on the arterial wall. Small tears in the wall expose the blood to foreign material and proteins which are highly thrombogenic. Resulting clots may grow gradually and may even contain growth hormones released by platelets within the clot. Moreover, growth hormones released by other cells, e.g., macrophages, may cause smooth muscle cells and fibroblasts in the affected region to multiply in an abnormal fashion. There may be an injury in the conduit wall due to the above methods that results in inflammation which may result in the growth of new tissue.

It is known that certain therapeutic substances may have a positive effect on prevention and/or inhibition of restenosis. Several difficulties present themselves in the application of these substances to the affected region in a therapeutic dose. For example, the region in need of treatment is very small and localized. Fluid, e.g., blood, flow in the conduit is continuous, resulting in a flow boundary along the wall which must be disrupted so that the therapeutic substances may reach the localized region of interest within a dose range considered therapeutic. The art fails to adequately provide a mechanism for breaking through this flow boundary to target the region of interest; electing instead generally to place the therapeutic substance into the general flow of the conduit, either by intravenous means or intra-lumen infusion, at a dose that is much higher than therapeutic since the majority of the therapeutic substance will simply flow downstream and either be absorbed systemically or eliminated as waste. For example, intravenous medications are delivered systemically by vein, or regionally, e.g., through intra-lumen infusion without targeting the subject region. Such unnecessary systemic exposure results with unknown and unnecessary adverse results in regions, tissue, and/or organs that are distant from the region of interest. Clearly, systemic delivery and exposure is not well suited to treatment of diseases or conditions having a single intra-lumen region of interest.

The potential utility of localized application of a therapeutic dose of therapeutic substances is not limited to treatment of coronary arteries. Beyond coronary artery delivery, other sites of atherosclerosis, e.g., renal, iliac, femoral, distal leg and carotid arteries, as well as saphenous vein grafts, synthetic grafts and arterio-venous shunts used for hemodialysis would be appropriate biological conduits for a localized therapeutic substance delivery method and mechanism. Nor is the potential utility limited to blood vessels; any biological conduit having a region of interest amenable to treatment may benefit from such a treatment method and mechanism.

The present invention overcomes these deficiencies.

BRIEF SUMMARY OF THE INVENTION

The invention provides a system, device and method for localized application of therapeutic substances within a biological conduit. In various embodiments, a dissolvable bag or bolus of at least one therapeutic agent is introduced and pressed and/or sealed against the wall of conduit. In other embodiments, dissolvable barbs formed from at least one therapeutic agent are ejected from a catheter by fluid pressure, embedding in the wall of conduit.

In this manner, application of at least one therapeutic dose of the therapeutic substance(s) at the affected region is achieved, while minimizing unwanted systemic exposure and the accompanying undesirable side effects. As a consequence, the need to administer super-therapeutic doses is eliminated.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

For the purposes of the present invention, the following terms and definitions apply:

"Bodily disorder" refers to any condition that adversely affects the function of the body.

The term "treatment" includes prevention, reduction, delay, stabilization, and/or elimination of a bodily disorder, e.g., a vascular disorder. In certain embodiments, treatment comprises repairing damage cause by the bodily, e.g., vascular, disorder and/or intervention of same, including but not limited to mechanical intervention.

A "therapeutic agent" comprises any substance capable of exerting an effect including, but not limited to therapeutic, prophylactic or diagnostic. Thus, therapeutic agents may comprise anti-inflammatories, anti-infectives, analgesics, anti-proliferatives, and the like including but not limited to antirestenosis drugs. Therapeutic agent further comprises mammalian stem cells. Therapeutic agent as used herein further includes other drugs, genetic materials and biological materials. The genetic materials mean DNA or RNA, including, without limitation, of DNA/RNA encoding a useful protein, intended to be inserted into a human body including viral vectors and non-viral vectors. Viral vectors include adenoviruses, gutted adenoviruses, adeno-associated virus, retroviruses, alpha virus, lentiviruses, herpes simplex virus, ex vivo modified cells (e.g., stem cells, fibroblasts, myoblasts, satellite cells, pericytes, cardiomyocytes, skeletal myocytes, macrophage), replication competent viruses, and hybrid vectors. Non-viral vectors include artificial chromosomes and mini-chromosomes, plasmid DNA vectors, cationic polymers, graft copolymers, neutral polymers PVP, SP1017, lipids or lipoplexes, nanoparticles and microparticles with and without targeting sequences such as the protein transduction domain (PTD). The biological materials include cells, yeasts, bacteria, proteins, peptides, cytokines and hormones. Examples for peptides and proteins include growth factors (FGF, FGF-1, FGF-2, VEGF, Endotherial Mitogenic Growth Factors, and epidermal growth factors, transforming growth factor .alpha.

and .beta., platelet derived endothelial growth factor, platelet derived growth factor, tumor necrosis factor .alpha., hepatocyte growth factor and insulin like growth factor), transcription factors, proteinkinases, CD inhibitors, thymidine kinase, and bone morphogenic proteins. These dimeric proteins can be provided as homodimers, heterodimers, or combinations thereof, alone or together with other molecules.

Therapeutic agents further includes cells that can be of human origin (autologous or allogeneic) or from an animal source (xenogeneic), genetically engineered, if desired, to deliver proteins of interest at the transplant site. Cells within the definition of therapeutic agents herein further include whole bone marrow, bone marrow derived mono-nuclear cells, progenitor cells (e.g., endothelial progenitor cells) stem cells (e.g., mesenchymal, hematopoietic, neuronal), pluripotent stem cells, fibroblasts, macrophage, and satellite cells.

Therapeutic agent also includes non-genetic substances, such as: anti-thrombogenic agents such as heparin, heparin derivatives, and urokinase; anti-proliferative agents such as enoxaprin, angiopeptin, or monoclonal antibodies capable of blocking smooth muscle cell proliferation, hirudin, and acetylsalicylic acid, amlodipine and doxazosin; anti-inflammatory agents such as glucocorticoids, betamethasone, dexamethasone, prednisolone, corticosterone, budesonide, estrogen, sulfasalazine, and mesalamine; antineoplastic/anti-proliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, taxol and its analogs or derivatives; anesthetic agents such as lidocaine, bupivacaine, and ropivacaine; anti-coagulants such as heparin, antithrombin compounds, platelet receptor antagonists, anti-thrombin anticodies, anti-platelet receptor antibodies, aspirin, dipyridamole, protamine, hirudin, prostaglandin inhibitors, platelet inhibitors and tick antiplatelet peptides; vascular cell growth promotors such as growth factors, Vascular Endothelial Growth Factors, growth factor receptors, transcriptional activators, and translational promoters; vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms; anti-oxidants, such as probucol; antibiotic agents, such as penicillin, cefoxitin, oxacillin, tobranycin angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme, inhibitors including captopril and enalopril. The biologically active material can be used with (a) biologically non-active material(s) including a solvent, a carrier or an excipient, such as sucrose acetate isobutyrate, ethanol, n-methyl pymolidone, dimethyl sulfoxide, benzyl benxoate and benzyl acetate.

Further, "therapeutic agent" includes, in particular in a preferred therapeutic method of the present invention comprising the administration of at least one therapeutic agent to a procedurally traumatized, e.g., by an angioplasty or atherectomy procedure, mammalian vessel to inhibit restenosis. Preferably, the therapeutic agent is a cytoskeletal inhibitor or a smooth muscle inhibitor, including, for example, taxol and functional analogs, equivalents or derivatives thereof such as taxotere, paclitaxel, abraxane™, coroxane™ or a cytochalasin, such as cytochalasin B, cytochalasin C, cytochalasin A, cytochalasin D, or analogs or derivatives thereof.

Additional specific examples of "therapeutic agents" that may be applied to a bodily lumen using various embodiments of the present invention comprise, without limitation:
L-Arginine;
Adipose Cells;
Genetically altered cells, e.g., seeding of autologous endothelial cells transfected with the beta-galactosidase gene upon an injured arterial surface;
Erythromycin;
Penicillin:
Heparin;
Aspirin;
Hydrocortisone;
Dexamethasone;
Forskolin;
GP IIb-IIIa inhibitors;
Cyclohexane;
Rho Kinsase Inhibitors;
Rapamycin;
Histamine;
Nitroglycerin;
Vitamin E;
Vitamin C;
Stem Cells;
Growth Hormones;
Hirudin;
Hirulog;
Argatroban;
Vapirprost;
Prostacyclin;
Dextran;
Erythropoietin;
Endothelial Growth Factor;
Epidermal Growth Factor;
Core Binding Factor A;
Vascular Endothelial Growth Factor;
Fibroblast Growth Factors;
Thrombin;
Thrombin inhibitor; and
Glucosamine, among many other therapeutic substances.

The therapeutic agent delivery system of the present invention can be used to apply the therapeutic agent to any surface of a body lumen where a catheter can be inserted. Such body lumen includes, inter alia, blood vessels, urinary tract, coronary vasculature, esophagus, trachea, colon, and biliary tract.

Figure 1:
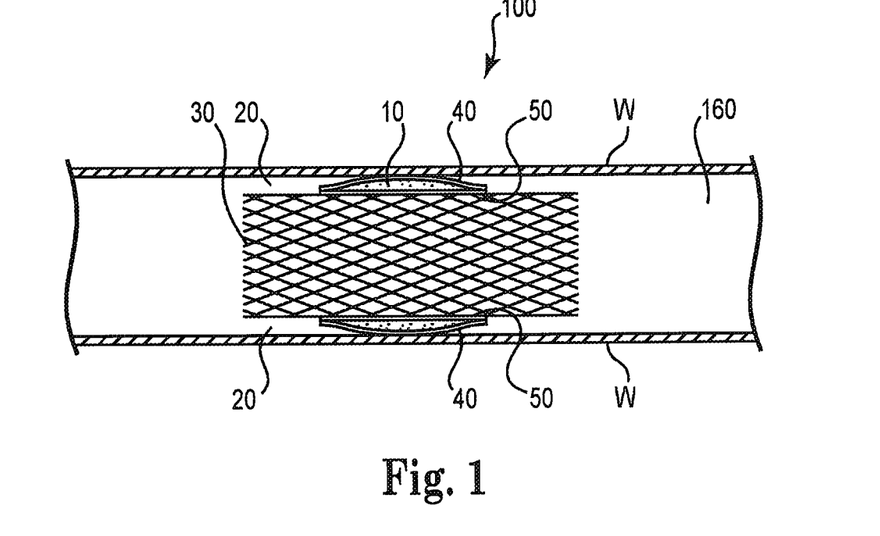
FIG. 1 is a side view of one embodiment of the present invention.

FIG. 1 illustrates one embodiment of a delivery system 100 for local delivery and application of at least one therapeutic agent 10 to a biological conduit 160. System 100 comprises a bag 20 comprising a dissolvable or biodegradable material and containing the at least one therapeutic agent 10, bag 20 is attached to the outer surface of an expandable stent 30; alternatively an expandable balloon may be used in place of stent 30. Bag 20 may wrap continuously radially around the external surface of expandable stent 30, or in a preferred embodiment, more than one bag 20 is placed radially around the external surface of the expandable stent 30. Stent 30 is expanded by any known method within biological conduit, pressuring dissolvable bag 20 with therapeutic agent(s) 10 therein against the inner surface of wall W of biological conduit. The bag 20 may be formed of two separate dissolvable or biodegradable materials: a first dissolvable or biodegradable material 40 on the conduit wall W side of the bag 20 and a second dissolvable or biodegradable material 50 on the stent side of the bag 20. Preferably, the first dissolvable or biodegradable material dissolves or biodegrades before the second dissolvable or biodegradable material dissolves or biodegrades. This differential arrangement of material allows the at least one therapeutic agent 10 access to the wall W of conduit 160 when the first material dissolves or biodegrades while the at least one therapeutic agent 10 is retained in place by stent and the second dissolvable or biodegradable material.

Figure 2A:
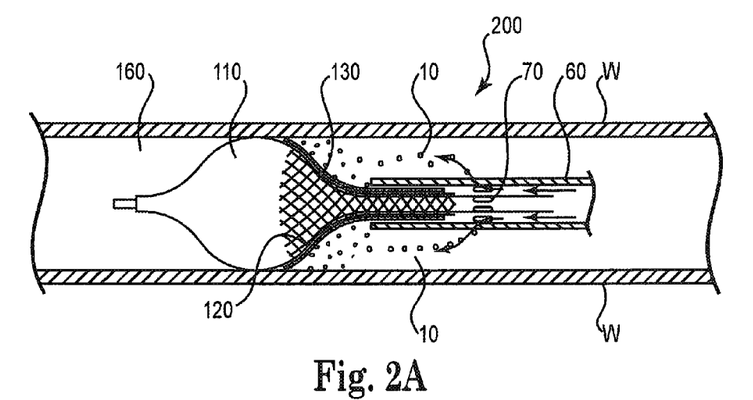
FIG. 2A is a side partial cutaway view of one embodiment of the present invention.
Figure 2B:
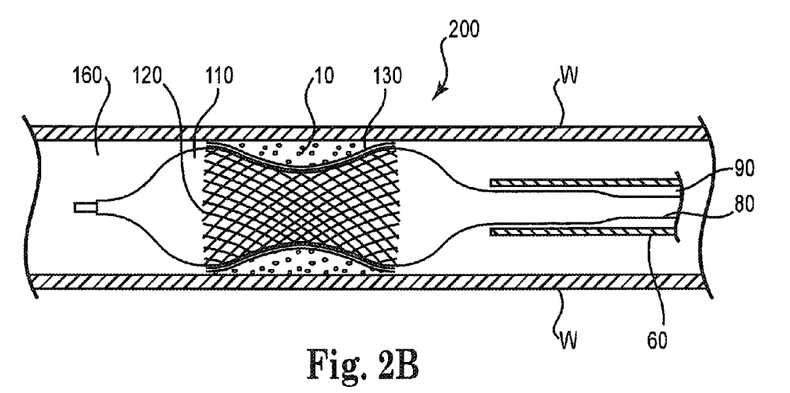
FIG. 2B is a side partial cutaway view of one embodiment of the present invention.
Figure 2C:
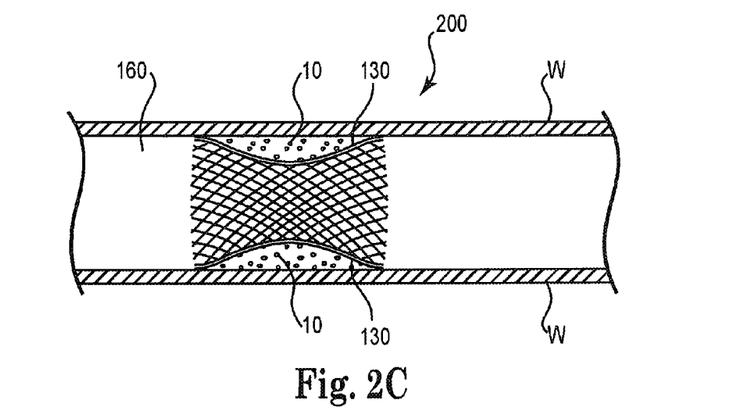
FIG. 2C is a side partial cutaway view of one embodiment of the present invention.

Turning now to FIGS. 2A-2C, another embodiment of a delivery system 200 for local delivery and application of at least one therapeutic agent 10 to a biological conduit 160. System 200 comprises a catheter 60 positioned within conduit 160 and comprising a lumen therethrough and a plurality of apertures 70 in fluid communication with conduit 160. Delivery sheath 80 is slidably disposed within the lumen of catheter 60. A therapeutic agent delivery lumen 90 is defined by the space between delivery sheath 80 and catheter 60. Delivery lumen 90 is in fluid communication with the plurality of apertures 70.

System 200 further comprises an inflatable balloon attached to the distal end of delivery sheath 80, inflatable balloon 110 inflated with inflation media and an inflation device as is well known in the art. Inflation balloon 110 is at least partially covered with an expandable stent 120, and expandable stent is covered with an expandable tube 130 comprised of plastic or comparable material. A syringe 170 comprising the at least one therapeutic agent 10 is in fluid communication with the therapeutic agent delivery lumen 90.

In operation, catheter 60 is positioned within conduit 160 and delivery sheath 80 positioned within catheter 60. Delivery sheath 80 is axially translated distally until the tip of the inflatable balloon 110 is outside of the lumen of catheter 60. The exposed tip of balloon 110 is then inflated with inflation media and the at least one therapeutic agent 10 is delivered under pressure down the therapeutic agent delivery lumen 90 until the agent(s) 10 reaches the plurality of apertures 70, where the agent(s) 10 are delivered to the biological conduit 160. At this point in the procedure, the delivery sheath 80 may be translated further distally, or alternatively, catheter 60 may be translated proximally. In either case, the remainder of the inflatable balloon 110 is translated distally outside of the lumen of catheter 60 and completely inflated, trapping the at least one therapeutic agent(s) between the wall W of conduit 160 and the expandable tube 130 covering stent 120. Inflatable balloon 110 may now be deflated and withdrawn, leaving stent 120, tube 130 and agent(s) 10 in place for therapeutic action.

Figure 3:
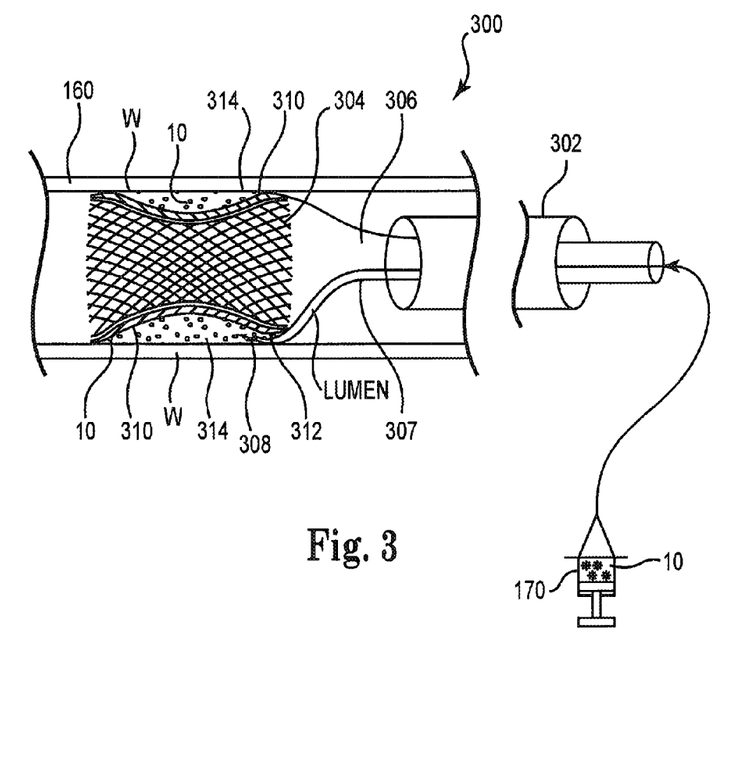
FIG. 3 is a side partial cutaway view of one embodiment of the present invention.

FIG. 3 provides another embodiment of a delivery system 300 for local delivery and application of at least one therapeutic agent 10 to a biological conduit 160. System 300 comprises an injection syringe 170 is well known in the art, wherein the at least one therapeutic agent 10 is stored. System 300 further comprises an elongated, flexible catheter 302, an expandable stent 304, expandable by means well known in the art including an inflatable balloon on catheter 302 or by self-expanding means, and an elongate, flexible delivery sheath 306 comprising a wall, the sheath wall 307 comprising a lumen therethrough, the lumen in fluid communication with injection syringe 170 and terminating in a flexible nozzle 308 which is in fluid communication with lumen of sheath wall 307. System 300 further comprises a distal expandable tubular region 310, wherein the flexible nozzle 308 is disposed on the external surface of the distal expandable tubular region 310, a bifurcation 312 of the sheath 306 defining the distal expandable tubular region 310 and the flexible nozzle 308.

In operation, the catheter 302, stent 304 and delivery sheath 306 are positioned at the region of interest within biological conduit 160. Stent 304 is expanded, as is the distal expandable tubular region 306, pressing distal expandable tubular region 306 and the flexible nozzle 308 against the wall W of biological lumen 160. The operator may then actuate syringe 170 to deliver the at least one therapeutic agent 10 through lumen of sheath wall 307 to flexible nozzle 308 where the agent(s) 10 is delivered, forming delivery pocket 314 radially around the expanded stent 304. At this point, the catheter 302 and sheath 306 may be removed, to allow the agent(s) to realize their therapeutic potential. In certain embodiments, the distal expandable tubular region 310 may detach from the delivery sheath 306, forming a barrier to hold the agent(s) within radial pocket 314 and to pressure the agent(s) generally uniformly against the wall W of biological conduit 160. Alternatively, the delivery sheath 306 is removed proximally in its entirety.

Figure 4:
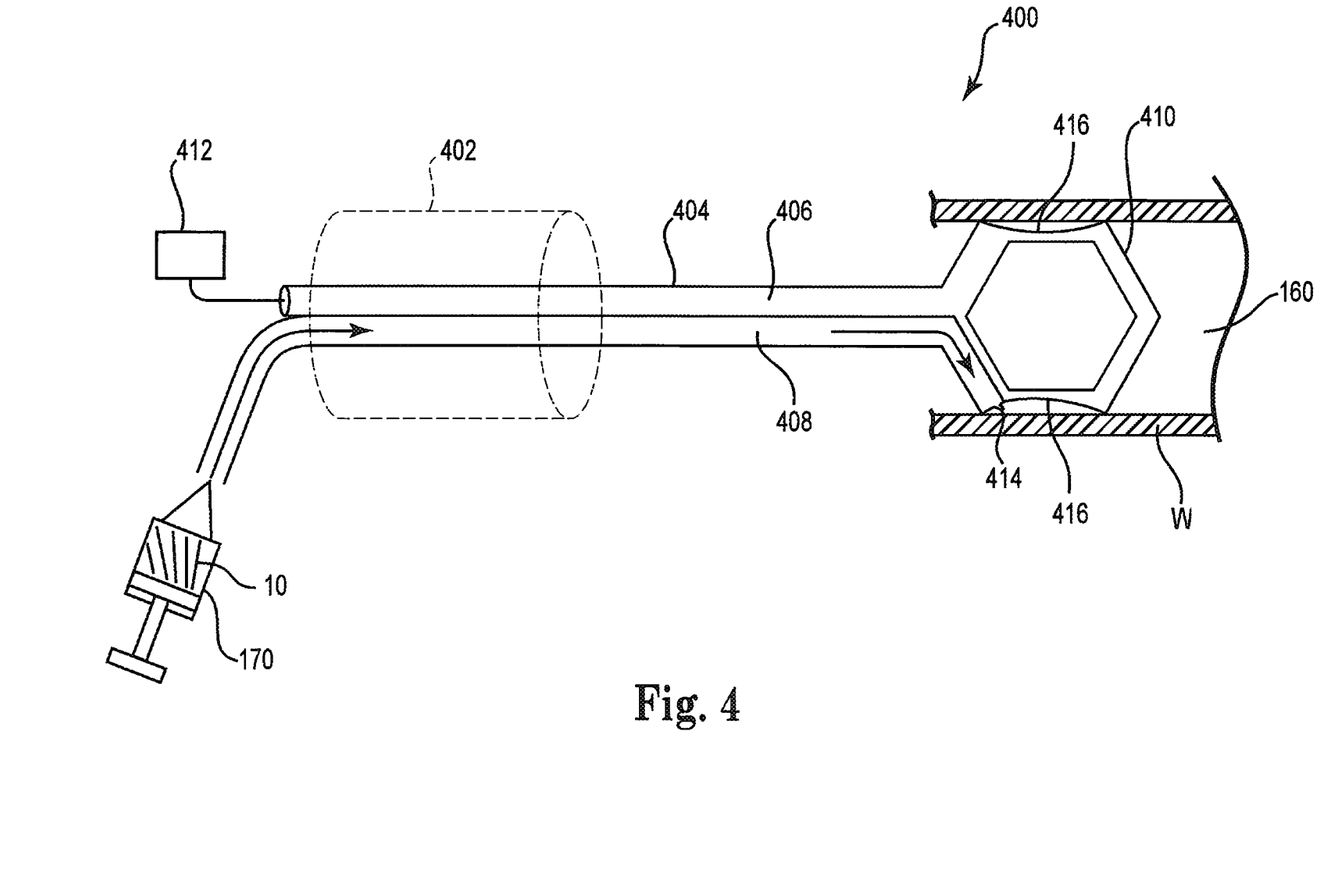
FIG. 4 is a side partial cutaway view of one embodiment of the present invention.

FIG. 4 illustrates another embodiment of a delivery system 400 for local delivery and application of at least one therapeutic agent 10 to a biological conduit 160. System 400 comprises a flexible, elongate catheter 402, slidingly positioned within conduit 160 and having a lumen therethrough. Inflatable delivery sheath 404 is slidingly disposed within lumen of catheter 402. Inflatable delivery sheath 404 comprises separate lumens therethrough, inflation lumen 406 and therapeutic agent delivery lumen 408. Inflatable delivery sheath 404 further comprises a distal inflatable balloon 410 in fluid communication with inflation lumen 406 and an inflation pump 412. Inflation lumen 408 terminates distally at an aperture 414 disposed in inflatable balloon 410, and is in fluid communication with a syringe 170, or the equivalent, containing the at least one therapeutic agent 10.

In operation, the catheter 402 is positioned within conduit 160, and inflatable delivery sheath 404 translated distally within lumen of catheter 402 until the deflated balloon 410 extends distally from the distal end of catheter 402. Inflation pump 412 is actuated, pumping inflation media through inflation lumen 406, thereby inflating inflatable balloon 410. Operator may then actuate syringe 170, delivering the at least one therapeutic agent 10 to the therapeutic agent delivery lumen 408 and through aperture 414, creating a thin therapeutic agent pocket 416 radially around inflated balloon 410, balloon 410 pressing therapeutic agent(s) 10 into wall W of conduit 160. The balloon 410 may then be deflated, retracted into lumen of catheter 402 and the device withdrawn.

Figure 5:
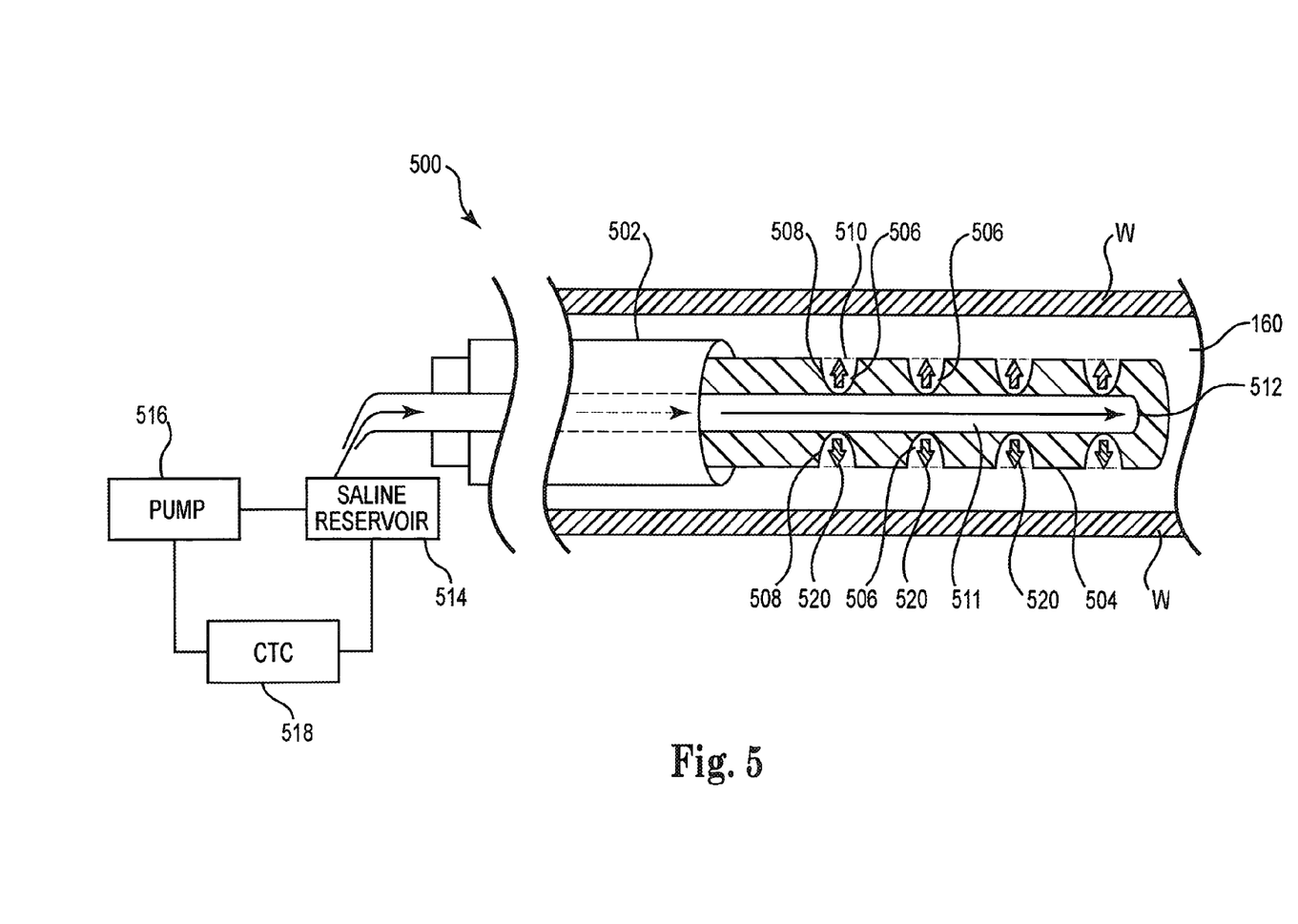
FIG. 5 is a side partial cutaway view of one embodiment of the present invention.
Figures 6, 7:
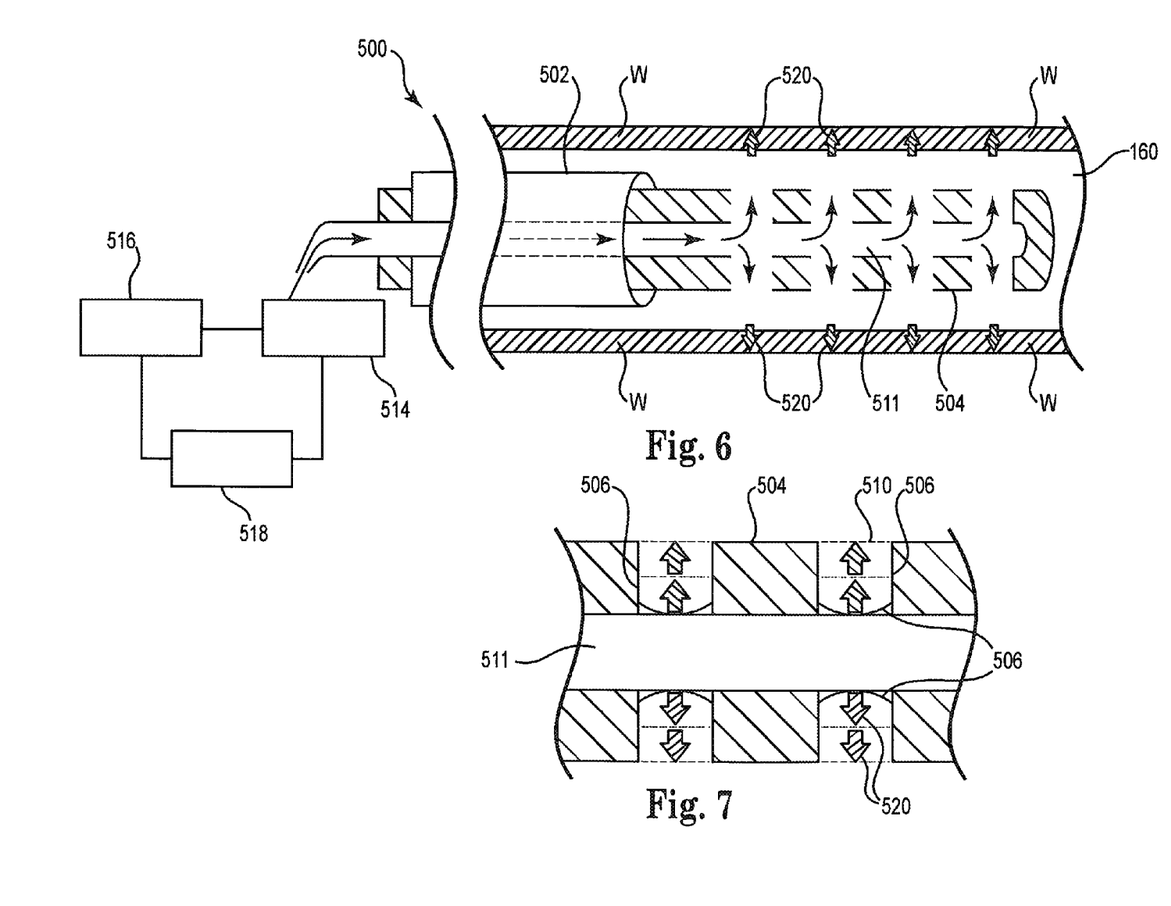
FIG. 6 is a side partial cutaway view of one embodiment of the present invention.
FIG. 7 is a side partial cutaway view of one embodiment of the present invention.

FIGS. 5-7 illustrate FIG. 4 illustrates another embodiment of a delivery system 500 for local delivery and application of at least one therapeutic agent 10 to a biological conduit 160. System 500 comprises a flexible elongate catheter 502 with a lumen therethrough. System 500 further comprises a delivery sheath 504 slidably disposed within lumen of catheter 502. A plurality of radially positioned pockets 506 are disposed near the distal end of delivery sheath 504. Pockets 506 are defined within delivery sheath 504 and by a thin base membrane 508 and thin cover membrane 510, thin base membrane 508 and thin cover membrane 510 each comprise very low fracture strength so that membranes 508, 510 may be easily broken. Delivery sheath 504 further comprise a fluid injection lumen 511 having a terminus 512 at its distal end and in fluid communication with a fluid reservoir 514, e.g., saline or the equivalent, fluid reservoir in operative connection and communication with a pump 416 for pumping the fluid into lumen 511. A control system 518 may be employed, providing control over the length of pumping time, the pressure of the pump, and the amount of fluid pumping through the lumen 511.

In this system 500, at least one therapeutic agent barb 520 is disposed within each pocket 506, held therein by the thin membranes 508, 510. Barb 520 may comprise frozen therapeutic agent(s) 10, or may be formed from a dissolvable or biodegradable material in the shape of a barb to facilitate entry into wall W of conduit, wherein the agent(s) 10 are disposed within the barb 520.

In operation, catheter 502 is positioned within conduit 160 and delivery sheath 504 slidably translated through lumen of catheter 502 until pockets 506 emerge distally from the lumen of catheter 502. Operator may then actuate the pump 516, either manually or via control system 518 in order to inject fluid from fluid reservoir 515 generate a rapid burst of fluid pressure into fluid injection lumen 511. Terminus 512 of fluid injection lumen 511 serves, in part, to force injected fluid to seek an exit from fluid injection lumen 511. This base membrane 508 is weak and, therefore, the pressure from the injected fluid breaks the membrane 508, pressuring the barb 520 radially outward in pocket 520. Cover membrane 510 is also easily broken by the radially outward pressuring of the barb 520 and fluid. Thus, the barbs 520 are ejected out of the pockets 506 and into wall W of conduit 160 as is best illustrated in FIG. 6.

FIG. 7 illustrates an alternate embodiment of system 500, wherein more than one barb 520 may be provided in pocket 506. Thus, a series of barbs 520 are provided in a radially stacked arrangement. The fluid injection through fluid injection lumen 511 may, in this embodiment, cause the barb 520 that is currently most radially outward to burst through its outer protective membrane 510. If desired, a second (or third, etc.) burst of injection fluid from reservoir 514 may be delivered to lumen 511, thereby injecting the next group of barbs 520. In this way, a succession of barbs 520 may be delivered to wall W of conduit 160 with successive bursts of injection fluid.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A system for local delivery and application of a bolus of at least one therapeutic agent to the inner wall of a biological conduit following a procedure to open the biological conduit by treating an occlusion therein, comprising:
    an expandable stent having an outer surface, the stent capable of delivery to the biological conduit and then expanding within the conduit; and
    a bag comprising a first dissolvable or biodegradable material and a second dissolvable or biodegradable material, the bag containing a dose of at least one therapeutic agent therein;
    wherein the bag is disposed on the outer surface of the expandable stent, the second dissolvable or biodegradable material is attached to, and wraps continuously radially around, the outer surface of the expandable stent, wherein the first dissolvable or biodegradable material is pressured and disposed against the inner wall of the biological conduit as a result of the pressuring of the expanding stent against the second dissolvable or biogradeable material,
    wherein the first dissolvable or biodegradable material dissolves or biodegrades before the second dissolvable or biodegradable material dissolves or biodegrades such that when the first dissolvable or biodegradable material dissolves or biodegrades, the dose of the at least one therapeutic agent is thereby exposed to the inner wall of the biological conduit, and
    wherein the pressure of the expanding stent against the second dissolvable or biodegradable material retains the dose of the at least one therapeutic agent in place to treat the trauma until the second dissolvable or biodegradable material dissolves or biodegrades.

2. The system of claim 1, wherein the at least one therapeutic agent comprises an antirestenosis drug.

3. The system of claim 2, wherein the antirestenosis drug comprises a cytoskeletal inhibitor.

4. The system of claim 2, wherein the antirestenosis drug comprises a smooth muscle inhibitor.

5. The system of claim 2, wherein the antirestenosis drug is selected from the group consisting of: taxol, taxotere, paclitaxel, abraxane, and coroxane.

6. The system of claim 1, wherein the at least one therapeutic agent is selected from the group consisting of an anticoagulant agent, an anti-proliferative agent, an anti-inflammatory agent, a vascular cell growth inhibitor, a cholesterol-lowering agent, a vasodilating agent, an anti-oxidant, an antibiogtic agent, digoxin, beta-blockers, angiotensin-converting enzyme, captopril, an anesthetic agent, and enalopril.

7. The system of claim 1, wherein the at least one therapeutic agent is selected from the group consisting of heparin, an antithrombin compound, a platelet receptor antagonist, an anti-thrombin antibodies, an anti-platelet receptor antibody, dipyridamole, protamine, hirudin, a prostaglandin inhibitor, a platelet inhibitor, a vascular cell growth promotor and urokinase.

8. The system of claim 1, wherein the at least one therapeutic agent is selected from the group consisting of enoxaparin, angiopeptin, monoclonal antibodies capable of blocking smooth muscle cell proliferation, hirudin, acetylsalicylic acid, amlodipine, and doxazosin.

9. The system of claim 1, wherein the at least one therapeutic agent is selected from the group consisting of glucocorticoids, betamethasone, dexamethasone, prednisolone, corticosterine, budesonide, estrogen, sulfasalazine, and mesalamine.

10. The system of claim 1, wherein the at least one therapeutic agent is selected from the group consisting of whole bone marrow, bone marrow derived mono-nuclear cells, progenitor cells, stem cells, pluripotent stem cells, fibroblasts, magrophages and satellite cells.

11. The system of claim 10, wherein the progenitor cells further comprise endothelial progenitor cells.

12. The system of claim 10, wherein the stem cells are selected from the group consisting of mesenchymal cells, hematopoietic cells and neuronal cells.

13. The system of claim 10, wherein the at least one therapeutic agent is selected from the group consisting of autologous origin cells, allogeneic origin cells, xenogeneic origin cells and genetically engineered cells.

14. The system of claim 1, wherein the at least one therapeutic agent is selected from the group consisting of DNA, RNA, viral vectors, and non-viral vectors.

15. The system of claim 1, wherein the at least one therapeutic agent is selected from the group consisting of cells, yeasts, bacteria, proteins, peptides, cytokines and hormones.

* * * * *